United States Patent [19]

O'Hanlon et al.

[11] 4,436,751

[45] Mar. 13, 1984

[54] NITROBENZYL MONATES ANTIBACTERIAL COMPOUNDS

[75] Inventors: Peter J. O'Hanlon, Redhill; Graham Walker, Guildford, both of England

[73] Assignee: Beecham Group Limited, England

[21] Appl. No.: 330,012

[22] Filed: Dec. 11, 1981

[30] Foreign Application Priority Data

Dec. 31, 1980 [GB] United Kingdom ................. 8041559
Aug. 18, 1981 [GB] United Kingdom ................. 8125168
Oct. 9, 1981 [GB] United Kingdom ................. 8130541

[51] Int. Cl.$^3$ ..................... A61K 31/35; C07D 309/10
[52] U.S. Cl. ..................................... 424/283; 542/427
[58] Field of Search ................. 260/345.8 R; 542/427; 424/283

[56] References Cited

U.S. PATENT DOCUMENTS 4,248,887 2/1981 Rogers et al. ................ 260/345.8 R
4,318,856 3/1982 Luk et al. ..................... 260/345.8 R

FOREIGN PATENT DOCUMENTS 54-151132 6/1979 Japan .
54-12376 7/1979 Japan .
1395907 5/1975 United Kingdom .

*Primary Examiner*—Nicky Chan
*Attorney, Agent, or Firm*—Jacobs & Jacobs

[57] ABSTRACT

Compounds of formula (II):

(II)

wherein

Y is —CH=CH—CH$_2$—CH— or $$-CH\underset{O}{-}CH-CH_2-CH-,$$

R$^1$ is hydrogen or C$_{1-4}$ alkyl,
R$^2$ is hydrogen or C$_{1-6}$ alkyl,
R$^3$ is hydrogen, nitro or C$_{1-6}$ alkyl and, when Y represents $$-CH\underset{O}{-}CH-CH_2-\overset{|}{C}H-$$

and R$^2$ and R$^3$ are hydrogen, the nitro radical is in the meta- or para- position on the benzene ring.

are novel and have antimycoplasmal activity. They may be produced by esterification of the corresponding carboxylic acid salt.

7 Claims, No Drawings

NITROBENZYL MONATES ANTIBACTERIAL COMPOUNDS

This invention relates to antibacterial compounds and in particular to a small class of esters which have antibacterial activity against certain Gram-positive and Gram-negative organisms, and also possess anti-mycoplasmal activity. The compounds are therefore of value in the treatment of human and veterinary infections.

U.K. Pat. No. 1,587,059 describes "monic acid A" and pharmaceutically acceptable esters thereof having the formula:

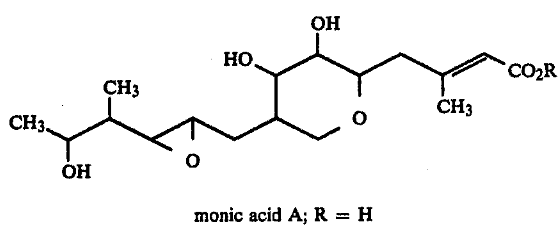

monic acid A; R = H

European Patent Application No. 0-005 006 describes "monic acid C" and pharmaceutically acceptable esters thereof having the formula:

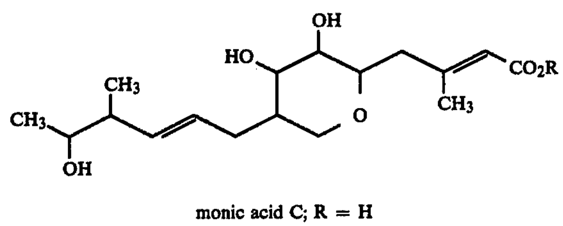

monic acid C; R = H

Japanese laid open Application No. 12376/79 discloses pseudomonic acid derivatives of the formula (I)

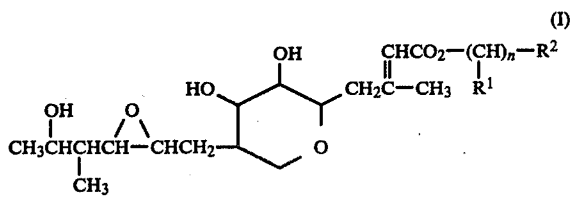

wherein $R^1$ represents hydrogen or lower alkyl, $R^2$ represents hydrogen, lower alkyl, lower alkenyl, lower alkynyl, lower alkoxy, lower alkoxycarbonyl, phenyl optionally substituted with 1-3 members of halogen, nitro, hydroxy, lower alkyl and lower alkoxy or a saturated or unsaturated heterocyclic group, and n represents an integer of 0-3. These derivatives are disclosed as having antibacterial efficacy against Gram-positive bacteria.

We have now surprisingly found that a small group of compounds, all within the broadest disclosure of the above U.K. or European patents, of which some also fall within the scope of the above Japanese Application, but are not specifically disclosed therein, have advantageous properties including outstanding antimycoplasmal and/or antibacterial activity which makes them particularly valuable in the treatment of mycoplasma-induced human or veterinary diseases.

Accordingly, the present invention provides an ester of formula (II):

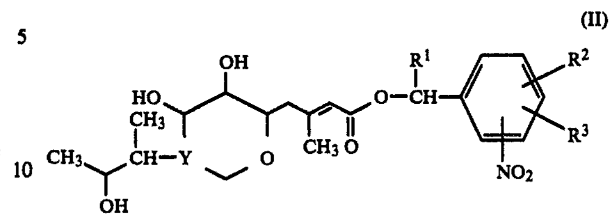

wherein Y is

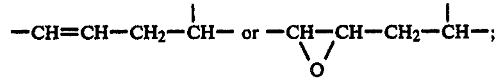

$R^1$ is hydrogen or $C_{1-4}$ alkyl, $R^2$ is hydrogen or $C_{1-6}$ alkyl, $R^3$ is hydrogen, nitro or $C_{1-6}$ alkyl and, when Y represents

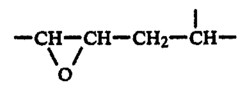

and $R^2$ and $R^3$ are hydrogen, the nitro radical is in the meta- or para- position on the benzene ring.

Preferably $R^1$ represents hydrogen or a methyl group. Preferably $R^2$ is hydrogen. Compounds of formula (II) wherein Y represents —CH=CH—CH₂—CH— are known as monate C esters, and those wherein Y represents

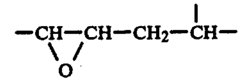

are known as monate A esters.

Particularly suitable compounds of the present invention include:

p-nitrobenzyl monate A
m-nitrobenzyl monate A
1-(m-nitrophenyl)ethyl monate A
1-(p-nitrophenyl)ethyl monate A
m-nitrobenzyl monate C
3,5-dinitrobenzyl monate A
3,5-dinitro-2-methylbenzyl monate A
2-methyl-3-nitrobenzyl monate A
3,4-dinitrobenzyl monate A
2,4-dinitrobenzyl monate A
2-chloro-4-nitrobenzyl monate A The infections against which compounds of this invention are particularly useful include venereal disease. They are also effective in the treatment of respiratory infections such as bacterial bronchitis; and bacterial meningitis, non-specific urethritis and pneumonia. In animals it may be employed for the treatment of mastitis in cattle, for swine dysentery, and for mycoplasma infections in animals such as turkeys, chickens, pigs and cattle.

Some of the human and veterinary diseases either caused by mycoplasma species or in which they play a prominent role, and against which compounds of this invention are effective, are as follows:

| | |
|---|---|
| Avian | |
| *M gallisepticum* | Chronic respiratory diseases (air-saccultitis) of chickens and turkeys |
| Bovine | |
| *M-bovis* | Mastitis, respiratory disease and arthritis of cattle |
| *M dispar* | Calf pneumonia |
| Porcine | |
| *M suipneumoniae* | Enzootic pneumonia of pigs |
| *M hyorhinis* | arthritis in pigs |
| *M hyosynoviae* | |

Human

M pneumoniae—primary atypical pneumonia

Compounds of the present invention are particularly useful in the treatment of enzootic pneumonia in animals such as pigs, cattle and sheep, because they also have activity against the bacteria *Bordetella bronchispetica, Pasteurella multocida* and Haemophilus spp, which often cause respiratory complications in cases of this disease.

Compounds of the present invention are also useful in the treatment of *Treponema hyodysenteriae* infections which cause swine dysentery.

This invention also provides a pharmaceutical or veterinary composition which comprises a compound of formula (II) together with a pharmaceutically or veterinary acceptable carrier or excipient.

The compositions may be formulated for administration by any route, and would depend on the disease being treated. The compositions may be in the form of tablets, capsules, powders, grandules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch, or acceptable wetting agents such as sodium lauryl sulphate. The tablets may be coated according to methods well known in normal pharmceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia; non aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin compounds of this invention may be made up into a cream, lotion or ointment. Cream or ointment formulations that may be used for compounds of formula (II) are conventional formulations well known in the art, for example, as described in standard text books of pharmaceutics and cosmetics, such as Harry's Cosmeticology published by Leonard Hill Books, and the British Pharmacopoeia.

Suppositories will contain conventional suppository bases, e.g. cocoa-butters or other glyceride.

For parenteral administration, fluid unit dosage forms are prepared utilizing the compound and a sterile vehicle. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lypophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compounds.

Veterinary compositions for intramammary treatment of mammary disorders in animals, especially bovine mastitis, will generally contain a suspension of a compound of formula (II) in an oily vehicle.

The compositions may contain from 0.1% to 99% by weight, preferably from 10–60% by weight, of the active material, depending on the method of administration. Where the compositions comprise dosage units, each unit will preferably contain from 50–500 mg, of the active ingredient. The dosage as employed for adult human treatment will preferably range from 100 mg to 3 g, per day, for instance 250 mg to 2 g, per day, depending on the route and frequency of administration.

Alternatively, a compound of formula (II) may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

A suitable method of administration of a compound of formula (II) to animals is to add it to the animals' drinking water. In this case a concentration of compound in the drinking water of about 5–500 μg/ml, for example 5–200 μg/ml, is suitable.

Compounds of formula (II) may be prepared by reacting a nitro-benzyl compound of formula (III):

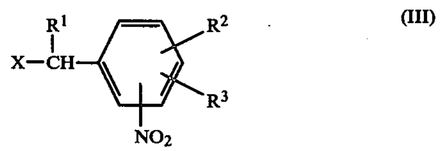

(III)

in which X is a good leaving group, preferably a halogen atom or an alkyl or aryl sulphonate, and $R^1$, $R^2$ and $R^3$ are as defined in formula (II) with a salt of an acid of formula (IV), preferably the sodium salt:

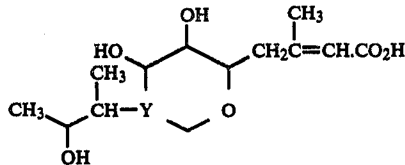

Preferably, X is a bromine atom or a mesylate group. The acid of formula (IV) wherein Y is

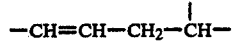

is known as monic acid C, and when Y is

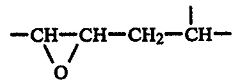

it is known as monic acid A.

The reaction is preferably carried out in an organic solvent, suitably dimethylformamide, at 20° C. to 100° C. and the resulting product may be purified chromatographically on silica.

The following Examples illustrate the preparation of compounds of the present invention.

EXAMPLE 1 p-Nitrobenzyl Monate A

A solution containing sodium monate A (1.1 g, 3 mmol) p-nitrobenzyl bromide (0.65 g, 3 mmol) and dimethyl formamide (35 ml) was stirred at 20° C. for 21 hr and then evaporated in vacuo. The residue was dissolved in ethyl acetate/brine, the oganic phase washed with aqueous sodium bicarbonate and then brine, dried (magnesium sulphate) and evaporated in vacuo. The resulting residue was purified by chromatography (0 to 6% methanol in dichloromethane, 20 g silicagel) to give the ester as a colourless oil (0.78 g, 55%)

i.r. spectrum: $\nu_{max}$ (film)

3400, 1710, 1640, 1600, 1520 $cm^{-1}$;

uv spectrum: $\lambda_{max}$ (EtOH)

216 nm ($\epsilon_m$=20,512), 263 nm ($\epsilon_m$=9,367);

$^1$H nmr: $\delta_H$ ($CDCl_3$)

8.22 and 7.54 (4H, ABq, aryl), 5.85 (1H, s, H2), 5.22 (2H, s, H1'), 2.23 (3H, s, $CH_3$-15), 1.21 (3H, d, $CH_3$-14), 0.93 (3H, d, $CH_3$-17);

$^{13}$C nmr: $\delta_C$ ($CDCl_3$)

166.0 (C1). 159.2 (C3), 147.6 (C1''), 143.9 (C4''), 128.3 (C3'', C5''), 123.7 (C2'', C6''), 116.5 (C2), 74.9 (C5), 71.1 (C13), 70.3 (C7), 68.9 (C6), 65.4 (C16), 64.0 (C1'), 61.2 (C11), 55.7 (C10), 43.0 (C4), 42.8 (C12), 39.6 (C8), 31.6 (C9), 20.7 (C14), 19.3 (C15), 12.6 (C17).

Trituration of this oil with petrol affords crystalline p-nitrobenzyl monate A, m.p. 95°–98° C.

EXAMPLE 2 m-Nitrobenzyl Monate A

A solution containing sodium monate A (0.73 g, 2 mmol), m-nitrobenzyl chloride (0.34 g, 2 mmol) and dimethyl formamide (25 ml) was stirred at 20° C. for 17 h and then evaporated in vacuo. The residue was taken up in ethyl acetate/brine, the organic phase washed with aqueous sodium bicarbonate and then brine, dried (magnesium sulphate) and evaporated in vacuo. The resulting residue was purified by chromatography (0 to 6% methanol in dichloromethane, 15 g silicagel) to give the ester as a colourless oil (0.63 g, 65%), i.r. spectrum: $\nu_{max}$ (film)

3400, 1710, 1640, 1530 $cm^{-1}$;

uv spectrum: $\lambda_{max}$ (EtOH)

219 nm ($\epsilon_m$=21,068);

$^1$H nmr: $\delta_H$ ($CDCl_3$)

8.35-7.30 (4H, m, aryl), 5.88 (1H, s, H2), 5.45 (2H, s, H1'), 2.25 (3H, s, $CH_3$-15), 1.21 (3H, d, $CH_3$-14), 0.93 (3H, d, $CH_3$-17).

EXAMPLE 3

1-(m-Nitrophenyl)ethyl monate A

A solution of sodium borohydride (0.4 g, 10 mmol) in ethanol (10 ml) was treated with m-nitroacetophenone (3.3 g, 20 mmol) at 20° C. for 20 mins. The solution was the diluted with aqueous potassium carbonate and extracted with chloroform. The extracts were dried (magnesium sulphate) and evaporated in vacuo to give 1-(m-nitrophenyl)ethanol as an oil (2.9 g, 90%);

i.r. spectrum: $\nu_{max}$ (film)

3400, 1530, 1350 $cm^{-1}$;

$^1$Hnmr: $\delta_H$ ($CDCl_3$)

7.3-8.3 (4H, m, aryl), 5.0 (1H, q, H1), 3.2 (1H, bs, OH), 1.5 (3H, s, H2).

The above alcohol (1.7 g, 10 mmol) and triphenylphosphine (2.8 g, 11 mmol) in carbon tetrachloride (10 mL) was heated at reflux for 1 h, and then cooled and filtered. The filtrate was treated with ether and filtered again, and then evaporated in vacuo to give 1-(m-nitrophenyl)ethyl chloride as a yellow oil (2.0 g, 100%) from which crystals of starting alcohol and triphenylphosphine oxide slowly separated;

i.r. spectrum: $\nu_{max}$ (film)

1530, 1350, 690 $cm^{-1}$;

$^1$Hnmr: $\delta_H$ ($CDCl_3$)

7.4-8.4 (4H, m, aryl), 5.2 (1H, q, H1), 1.8 (3H, d, H2).

A mixture containing sodium monate A (1.1 g, 3 mmol) and 1-(m-nitrophenyl)ethyl chloride (0.4 g, 2 mmol) in dimethyl formamide (30 mL) was stirred at 50° C. for 4 h and then evaporated in vacuo. The residue was dissolved in ethyl acetate, which was washed with aqueous sodium bicarobate, dried (magnesium sulphate) and evaporated in vacuo, and the resulting residue purified by chromatography (20 g silica, 0 to 6% methanol in dichloromethane) to give 1-(m-nitrophenyl)ethyl monate A as a colourless oil (0.11 g, 11%);

i.r. spectrum: $\nu_{max}$ (film)

3450, 1715, 1645, 1530, 1350 $cm^{-1}$;

uv spectrum: $\lambda_{max}$ (EtOH)

219 nm ($\epsilon_m$ 18,500), 258 (sh, $\epsilon_m$ 6,500);

$^1$H nmr: $\delta_H$ ($CDCl_3$)

8.24 (1H, s, H2''), 8.13 (1H, d, H4''), 7.69 (1H, d, H6''), 7.50 (1H, dd, H5''), 5.95 (1H, q, H1'), 5.83 (1H, s, H2), 2.20 (3H, s, $CH_3$-15), 1.49 (3H, d, H2'), 1.20 (3H, d, $CH_3$-14), 0.90 (3H, d, $CH_3$-17);

$^{13}$C nmr: $\delta_C$ ($CDCl_3$)

165.5 (C1), 158.4 (C3), 148.6 (C3''), 144.5 (C1''), 132.3 (C6''), 129.5 (C5''), 122.7 (C4''), 121.1 (C2''), 117.1, 117.2 (C2), 75.0 (C5), 71.3 (C1'), 70.5 (C13), 70.3 (C7), 69.1 (C6), 65.4 (C16), 61.3 (C11), 55.5 (C10), 43.0 (C12), 42.9 (C4), 39.7 (C8), 31.7 (C9), 22.3 (C2'), 20.8 (C14), 19.3, 19.2 (C15), 12.6 (C17);

m/e (relative intensity)

(C.I. $NH_3$) 494 (MH+, 1%), 227 (31), 150 (100)

EXAMPLE 4

1-(p-Nitrobenzyl)ethyl monate A p-Ethylnitrobenzene (4.0 ml, 0.03 mmol) heated to 130° C. was treated with bromine (1.5 mL, 0.03 mmol). A vigorours reaction took place and hydrogen bromide was evolved. When the reaction was complete the residue in the flask was identified as 1-(p-nitrophenyl)ethyl bromide (6.3 g, 100%);

$^1$H nmr: $\delta_H$ ($CDCl_3$)
8.2 (2H, d, H3', H5'), 7.6 (2H, d, H2', H6'), 5.2 (1H, q, H1), 2.0 (3H, d, H2).

A solution containing sodium monate A (1.46 g, 4 mmol) 1-(p-nitrophenyl)ethyl bromide (0.92 g, 4 mmol) and dimethyl formamide (20 mL) was stirred at 20° C. for 4 h and then evaporated in vacuo. The residue was dissolved in ethyl acetate, which was then washed with aqueous sodium bicarbonate, dried (magnesium sulphate) and evaporated in vacuo. The resulting residue was purified by chromatography (30 g silica, 0 to 8% methanol in dichloromethane), to give 1-(p-nitrophenyl) ethyl monate A as a yellowish oil (1.36 g, 70%);

i.r. spectrum: $\nu_{max}$ (film)
3400, 1710, 1645, 1605 cm$^{-1}$;

uv spectrum: $\lambda_{max}$ (EtOH)
219 nm ($\epsilon_m$ 24,600), 265 nm ($\epsilon_m$ 14,100);

$^1$H nmr: $\delta_H$ ($CDCl_3$)
8.20 (2H, d, H3", H5"), 7.63 (2H, dd, H2", H6"), 5.94 (1H, q, H1'), 5.82 (1H, s, H2), 2.20 (3H, s, $CH_3$-15), 1.56 (3H, d, H2'), 1.20 (3H, d, $CH_3$-14), 0.90 (3H, d, $CH_3$-17);

$^{13}$C nmr: $\delta_C$ ($CDCl_3$)
165.5 (C1), 158.7 (C3), 149.6, 149.5 (C4"), 147.3 (C1"), 126.8, 126.7 (C2", C6"), 123.7 (C3", C5"), 116.9, 116.8 (C2), 74.8 (C5), 71.2 (C1'), 70.4 (C13), 70.3 (C7), 68.9 (C6), 65.4 (C16), 61.2 (C11), 55.6 (C10), 43.0 (C12), 42.8 (C4), 39.6 (C8), 31.6 (C9), 22.3 (C2'), 20.7 (C14), 19.2, 19.1 (C15), 12.6 (C17);

m/e (relative intensity)
493 (M+, 1%), 325 (10), 227 (58), 150 (89), 44 (100)

EXAMPLE 5 m-Nitrobenzyl monate C

Monic acid C (1 mmol, 0.33 g) was dissolved in methanol (10 ml) and sodium bicarbonate (0.84 g, 1 mmol) added and stirred for ½ h. After evaporation in vacuo, m-nitrobenzyl chloride (0.17 g, 1 mmol) and DMF (10 ml) were added and stirred at 20° overnight. The reaction mixture was evaporated in vacuo, and the residue taken up in ethyl acetate/brine. The organic layer was washed with aqueous sodium bicarbonate, then brine, dried ($MgSO_4$) and evaporated in vacuo. The resulting residue was purified by chromatography, (10 g silica gel, 0 to 4% methanol in dichloromethane) to yield the ester as a colourless oil (208 mg, 50%);

i.r. spectrum: $\nu_{max}$ ($CHCl_3$)
3445, 1710, 1670, 1640, 1530 cm$^{-1}$;

uv spectrum: $\lambda_{max}$ (EtOH)
216 nm ($\epsilon_m$ 20,575), 254 nm ($\epsilon_m$ 7,385);

$^1$H nmr: $\delta_H$ ($CDCl_3$)
8.25 (1H, s, H2"), 8.18 (1H, d, H4"), 7.71 (1H, d, H6"), 7.55 (1H, t, H5"), 5.87 (1H, s, H2), 5.21 (2H, s, $CH_2$-1'), 2.24 (3H, s, $CH_3$-15), 1.17 (3H, d, $CH_3$-14), 0.98 (3H, d, $CH_3$-17).

$^{13}$Cnmr: $\delta_C$ ($CDCl_3$)
166.0 (C1), 159.1 (C3), 148.6 (C3"), 138.8 (C1"), 134.5, 133.8 (C1"), 134.5, 133.8, 129.5, 129.3 (C5", 6", 10, 11), 122.9, 122.8 (C2", 4"), 116.7 (C2), 75.0 (C5), 71.3 (C13), 70.5 (C7), 69.0 (C6), 64.9 (C16), 64.1 (C1'), 44.6 (C12), 43.3 (C4), 42.2 (C8), 32.4 (C9), 20.4 (C14), 19.4 (C15), 16.6 (C17).

EXAMPLE 6

3,5-Dinitrobenzyl monate A

A solution containing sodium monate A (0.73 g, 2 mmol), 3,5-dinitrobenzyl chloride (0.44 g, 2 mmol) in dimethyl formamide (25 ml) was stirred at 20° C. for 18 h and evaporated in vacuo. The residue was taken up in ethyl acetate/brine, the organic phase washed with aqueous sodium bicarbonate and then brine, dried (magnesium sulphate), and then evaporated in vacuo. The resulting residue was purified by chromatography (0 to 6% methanol in dichloromethane, on 15 g silicagel) to yield 3,5-dinitrobenzyl monate A as a white solid, m.p. 122°-124° C. (543 mg, 52%);

i.r. spectrum $\nu_{max}$ (film)
3480, 3280, 3110, 1720, 1650, 1540 cm$^{-1}$;

uv spectrum: $\lambda_{max}$ (EtOH)
227 nm ($\epsilon_m$ 30,984);

$^1$H nmr: $\delta_H$ ($CDCl_3$)
9.00 (1H, s, H4"), 8.58 (2H, s, H2", H6"), 5.88 (1H, s, H2), 5.33 (2H, s, H1'), 2.25 (3H, s, $CH_3$-15), 1.23 (3H, d, $CH_3$-14), 0.91 (3H, d, $CH_3$-17);

$^{13}$C nmr: $\delta_C$ ($CDCl_3$)
165.6 (C1), 160.3 (C3), 148.8 (C1"), 141.4 (C3", C5"), 127.8 (C2", C6"), 118.3 (C4"), 116.1 (C2), 75.0 (C5), 71.4 (C13), 70.5 (C7), 69.1 (C6), 65.5 (C16), 63.1 (C1'), 61.3 (C11), 55.6 (C10), 43.1 (C4), 42.9 (C12), 39.8 (C8), 31.7 (C9), 20.8 (C14), 19.5 (C15), 12.7 (C17);

microanalysis: (Found C: 54.70, H: 5.49, N: 5.34%, $C_{24}H_{32}N_2O_{11}$ requires C: 54.96, H: 6.11, N: 5.34%).

EXAMPLE 7

3,5-Dinitro-2-methylbenzyl monate A

To a solution containing 3,5-dinitro-2-methylbenzyl alcohol (0.64 g, 3 mmol) in dichloromethane (15 ml) with triethylamine (0.5 ml, 3.5 mmol) at −10° C. was added mesyl chloride (0.3 ml, 4 mmol). The mixture was stirred for ca ½ h and poured into water. The organic layer was washed with aqueous sulphuric acid, aqueous sodium bicarbonate and then brine, dried (magnesium sulphate), evaporated in vacuo and added to a solution of sodium monate A (0.73 g, 2 mmol) in dimethyl formamide (10 ml). The mixture was stirred at 20° C. for 19 h and evaporated in vacuo. The residue was taken up in ethyl acetate, which was washed with brine, aqueous sodium bicarbonate and then more brine, dried (magnesium sulphate) and evaporated in vacuo. The residual oil was purified by chromatography (0 to 6% methanol in dichloromethane, on 10 g silicagel) to yield 3,5-dinitro-2-methylbenzyl monate A as a pale yellow oil (70 mg, 6%).

i.r. spectrum: $\nu_{max}$ (film)
3400, 1720, 1640, 1535 cm$^{-1}$;

uv spectrum: $\lambda_{max}$ (EtOH)
224 nm ($\epsilon_m$ 19.314);

$^1$H nmr: $\delta_H$ ($CDCl_3$)
8.60 (1H, d, H4"), 8.46 (1H, d, H6"), 5.88 (1H, s, H2), 5.27 (2H, s, H1'), 2.57 (3H, s, $CH_3$-7"), 2.26 (3H, s, $CH_3$-15), 1.22 (3H, d, $CH_3$-14), 0.95 (3H, d, $CH_3$-17);

$^{13}$C nmr: $\delta_C$ ($CDCl_3$)

165.5 (C1), 160.1 (C3), 146.0 (C1″), 140.1 (C3″, C5″), 137.8 (C2″), 126.2 (C6″), 118.8 (C4″), 116.2 (C2), 75.0 (C5), 71.4 (C13), 70.6 (C7), 69.1 (C6), 65.4 (C16), 62.1 (C1′), 61.3 (C11), 55.5 (C10), 43.1 (C4), 42.9 (C12), 39.8 (C8), 31.7 (C9), 20.9 (C14), 19.5 (C15), 15.1 (C7″), 12.7 (C17);

Mass spectrum: m/e (relative intensity) 538 (M+, 1%), 476 (8), 323 (10), 227 (100).

EXAMPLE 8

2-Methyl-3-nitrobenzyl monate A

A solution containing sodium monate A (0.73 g, 2 mmol), 2-methyl-3-nitrobenzyl chloride (0.37 g, 2 mmol), and dimethyl formamide (25 ml) was stirred at room temperature for 17 h and then evaporated in vacuo. The residue was then taken up in ethyl acetate/-brine, washed with aqueous sodium bicarbonate, then brine, dried (magnesium sulphate), and evaporated in vacuo. The resulting residue was purified by chromatography (0 to 4% methanol in dichloromethane) on 8 g silicagel) to yield 2-methyl-3-nitrobenzyl monate A as a pale yellow oil (619 mg, 63%);

i.r. spectrum: $\nu_{max}$ (film)
 3440, 1710, 1650, 1530 $cm^{-1}$;

uv spectrum: $\lambda_{max}$ (EtOH)
 221 nm ($\epsilon_m$ 20,926);

$^1H$ nmr $\delta_H$ $(CDCl_3)$
 7.75 (1H, d, H4″), 7.60 (1H, d, H6″), 7.32 (1H, t, H5″), 5.82 (1H, s, H2), 5.20 (2H, s, $CH_2$-1′), 2.48 (3H, s, $CH_3$-7″), 2.24 (3H, s, $CH_3$-15), 1.23 (3H, d, $CH_3$-14), 0.94 (3H, d, $CH_3$-17);

$^{13}C$ nmr: $\delta_C$ $(CDCl_3)$
 166.0 (C1), 158.9 (C3), 151.2 (C3″), 137.3 (C1″), 133.2 (C6″), 131.3 (C2″), 126.5 (C5″), 123.9 (C4″), 116.6 (C2), 74.9 (C5), 71.2 (C13), 70.3 (C7), 69.0 (C6), 65.5 (C16), 63.2 (C1′), 61.2 (C11), 55.6 (C10), 42.9 (C4), 42.8 (C12), 39.6 (C8), 31.6 (C9), 20.8 (C14), 19.2 (C15), 14.6 (C7″), 12.6 (C17);

mass spectrum: m/e (relative intensity) 493 (M+, 0.34%), 227 (39), 223 (21), 150 (100) (Found: M+, 493.2349. $C_{25}H_{35}NO_9$ requires 493.2309).

EXAMPLE 9

3,4-Dinitrobenzyl monate A 3,4-Dinitrobenzyl alcohol (0.6 g, 3 mmol), acetic acid (10 ml) and a solution of hydrobromic acid in acetic acid (45% w/v HBr, 1 ml, 6 mmol) were heated under reflux for 17 h. The reaction mixture was then evaporated in vacuo, and added to sodium monate A (1.1 g, 3 mmol), sodium bicarbonate (0.5 g) and dimethyl formamide (30 ml). The solution was stirred at 20° C. for 18 h and then evaporated in vacuo. The residue was taken up in ethyl acetate/brine, washed with aqueous sodium bicarbonate, then brine, dried (magnesium sulphate) and evaporated in vacuo. The resulting residue was purified by chromatography (10 g silicagel, 0 to 4% methanol in dichloromethane) to yield 3,4-dinitrobenzyl monate A (402 mg, 26%);

i.r. spectrum: $\nu_{max}$ (film)
 3440, 1720, 1645, 1550 $cm^{-1}$;

uv spectrum: $\lambda_{max}$ (EtOH)
 225 nm ($\epsilon_m$ 24,139);

$^1H$ nmr: $\delta_H$ $(CDCl_3)$
 8.1-7.65 (3H, m, aryl), 5.85 (1H, s, H2), 5.25 (2H, s, $CH_2$), 2.24 (3H, s, $CH_3$-15), 1.23 (3H, d, $CH_3$-14), 0.94 (3H, d, $CH_3$-17);

$^{13}C$ nmr: $\delta_C$ $(CDCl_3)$
 165.6 (C1), 160.3 (C3), 144.1 (C1″), 143.1, 141.9, 132.1, 125.5, 123.9 (C2″, 3″, 4″, 5″, 6″), 116.0 (C2), 74.9 (C5), 71.2 (C13), 70.4 (C7), 69.0 (C6), 65.4 (C16), 63.0 (C1′), 61.3 (C11), 55.7 (C10), 43.0 (C4), 43.8 (C12), 39.7 (C8), 31.6 (C9), 20.8 (C14), 19.4 (C15), 12.6 (C17).

EXAMPLE 10

2,4-Dinitrobenzyl monate A

Sodium borohydride (0.2 g, 10 mmol) in ethanol (40 ml) was added dropwise to 2,4-dinitrobenzaldehyde (1.96 g, 10 mmol) in ethanol (40 ml) and stirred for 1 h. The reaction mixture was then evaporated in vacuo, partitioned between ether and aqueous sodium bicarbonate, the ether layer dried (magnesium sulphate) and evaporated in vacuo to yield 2,4-dinitrobenzyl alcohol as a brown solid (1.147 g, 58%), m.p. 105°-110° C.;

$^1H$ nmr: $\delta_H$ $(CDCl_3)$
 9.0-8.1 (3H, m, aryl), 5.18 (2H, s, $CH_2$), 2.4 (1H, s, OH).

2,4-Dinitrobenzyl alcohol (1.15 g, 5 mmol), acetic acid (10 ml) and a solution of hydrobromic acid in acetic acid (45% w/v HBr, 2 ml, 12 mmol) were heated under reflux for 18 h. The reaction mixture was evaporated in vacuo, and sodium monate A (1.8 g, 5 mmol) and dimethyl formamide (30 ml) added and stirred at 20° C. for 18 h. The reaction mixture was then evaporated in vacuo, taken up in ethyl acetate, washed with aqueous sodium bicarbonate and then brine, dried (magnesium sulphate) and evaporated in vacuo. The residual oil was purified by chromatography (15 g silicagel, 0 to 4% methanol in dichloromethane) to yield 2,4-dinitrobenzyl monate A as a pale yellow oil (1.31 g, 50%);

i.r. spectrum: $\nu_{max}$ (film)
 3440, 1720, 1660, 1610, 1480 $cm^{-1}$;

uv spectrum: $\lambda_{max}$ (EtOH)
 226 nm ($\epsilon_m$ 22,792);

$^1H$ nmr: $\delta(CDCl_3)$
 8.95 (1H, d, H3″), 8.50 (1H, dd, H5″), 7.90 (1H, d, H6″), 5.90 (1H, s, H2), 5.60 (2H, s, $CH_2$-1′), 2.24 (3H, s, $CH_3$-15), 1.21 (3H, d, $CH_3$-14), 0.93 (3H, d, $CH_3$-17).

EXAMPLE 11

2-Chloro-4-nitrobenzyl monate A

2-Chloro-4-nitrobenzyl bromide (0.50 g, 2 mmol), sodium monate A (0.73 g, 2 mmol) and dimethyl formamide (20 ml) were stirred at 20° C. for 16½ h and then evaporated in vacuo. The residue was taken up in ethyl acetate/brine, washed with aqueous sodium bicarbonate, then brine, dried (magnesium sulphate) and evaporated in vacuo. The resulting residue was purified by chromatography (10 g silicagel, 0 to 4% methanol in dichloromethane) to yield 2-chloro-4-nitrobenzyl monate A (239 mg, 23%) m.p. 101°-103° C.

i.r. spectrum: $\nu_{max}$(KBr)
 3445, 1720, 1650, 1520 $cm^{-1}$;

uv spectrum: $\lambda_{max}$ (EtOH)
 216 nm ($\epsilon_m$ 28,331);

$^1H$ nmr: $\delta_H$ $(CDCl_3)$
 8.27 (1H, d, H3″), 8.15 (1H, dd, H5″), 7.64 (1H, d, H6″), 5.90 (1H, s, H2), 5.32 (2H, s, $CH_2$-$1^1$), 2.25 (3H, s, $CH_3$-15), 1.23 (3H, d, $CH_3$-14), 0.96 (3H, d, $CH_3$-17);

$^{13}C$ nmr: $\delta_C$ $(CDCl_3)$
 165.6 (C1), 159.5 (C3), 148.0 (C1″), 141.7 (C4″), 133.9 (C2″), 129.4 (C3″), 124.6 (C6″), 121.9 (C5″), 116.4 (C2), 75.1 (C5), 71.3 (C13), 70.5 (C7), 69.1 (C6), 65.5 (C16), 61.9 ($C1^1$), 61.3 (C11), 55.6 (C10), 43.1

(C12), 42.9 (C4), 39.8 (C8), 31.7 (C9), 20.8 (C14), 19.5 (C15), 12.7 (C17);

microanalysis: Found: C 56.16, H 5.97, N 2.66%, $C_{24}H_{32}NO_9Cl$ requires: C 56.09; H 6.23; N 2.73%.

Biological Data

The compounds of the present invention were screened for anti-mycoplasmal and anti-bacterial activity, and the results were compared with the structurally closely related compound O-nitrobenzyl monate A.

| Example No. | Compound |
|---|---|
| 1 | p-nitrobenzyl monate A |
| 2 | m-nitrobenzyl monate A |
| 3 | 1-(m-nitrophenyl)ethyl monate A |
| 4 | 1-(p-nitrophenyl)ethyl monate A |
| 5 | m-nitrobenzyl monate C |
| 6 | 3,5-dinitrobenzyl monate A |
| 7 | 3,5-dinitro-2-methylbenzyl monate A |
| 8 | 2-methyl-3-nitrobenzyl monate A |
| 9 | 3,4-dinitrobenzyl monate A |
| 10 | 2,4-dinitrobenzyl monate A |

-continued

| Example No. | Compound |
|---|---|
| 11 | 2-chloro-4-nitrobenzyl monate A |
| "C" | O—nitrobenzyl monate A for comparison |

(a) Anti-Mycoplasmal Activity

Table 1 shows the in vitro MIC values (μg/ml) of the compounds of the Examples against a number of mycoplasma organisms. The values were determines in Friis broth solidified with 0.9% agarose. The inoculum was $10^3$ to $10^5$ C.F.U. and the MIC's were recorded after 6 days incubation at 37° C.

TABLE 1

| ORGANISMS | EXAMPLE NO - MIC (μg/ml) 1 | 2 | 3 | 4 | 5 | 6 | 7 | 8 | 9 | 10 | 11 | C |
|---|---|---|---|---|---|---|---|---|---|---|---|---|
| *M. suipneumoniae* NB12 | 0.05 | 0.025 | 0.25 | 1.0 | 0.25 | 0.05 | 0.25 | 0.1 | 0.25 | 1.0 | 1.0 | 0.5 |
| *M. suipneumoniae* JF 435 | 0.1 | 0.025 | 0.25 | 2.5 | 0.25 | 0.05 | 0.25 | 0.1 | 1.0 | 1.0 | 2.5 | 0.5 |
| *M. suipneumoniae* HR(2) | 0.1 | 0.025 | 0.25 | 2.5 | 0.25 | 0.05 | 0.25 | 0.1 | 0.5 | 1.0 | 2.5 | 0.5 |
| *M. suipneumoniae* Str. 11 | 0.05 | 0.025 | 0.1 | 1.0 | 0.1 | 0.025 | 0.1 | 0.1 | 0.25 | 0.5 | 1.0 | 0.25 |
| *M. suipneumoniae* J2206/183b | 0.1 | 0.025 | 0.25 | 1.0 | 0.25 | 0.05 | 0.25 | 0.25 | 1.0 | 1.0 | 1.0 | 0.5 |
| *M. suipneumoniae* MS 16 | 0.05 | ≦0.01 | 0.1 | 1.0 | 0.1 | 0.025 | 0.1 | 0.1 | 0.25 | 0.5 | 1.0 | 0.25 |
| *M. suipneumoniae* PW/C/210 | 0.05 | ≦0.01 | 0.1 | 1.0 | 0.1 | 0.025 | 0.1 | 0.1 | 0.25 | 0.5 | 1.0 | 0.25 |
| *M. suipneumoniae* LABER | 0.05 | 0.025 | 0.1 | 1.0 | 0.1 | 0.025 | 0.1 | 0.1 | 0.25 | 0.5 | 1.0 | 0.25 |
| *M. suipneumoniae* OCD 1 | 0.1 | 0.025 | 0.25 | 1.0 | 0.25 | 0.05 | 0.25 | 0.25 | 0.5 | 1.0 | 2.5 | 0.5 |
| *M. suipneumoniae* TAM 6N | 0.1 | 0.025 | 0.25 | 2.5 | 0.25 | 0.05 | 0.25 | 0.25 | 0.5 | 1.0 | 2.5 | 0.5 |
| *M. suipneumoniae* ATCC 25095 | 0.05 | 0.025 | 0.1 | 1.0 | 0.25 | 0.05 | 0.25 | 0.1 | 0.25 | 0.5 | 1.0 | 0.25 |
| *M. suipneumoniae* NCTC 10110 | 0.05 | 0.025 | 0.25 | 2.5 | 0.25 | 0.05 | 0.25 | 0.1 | 0.5 | 1.0 | 1.0 | 0.5 |
| *M. hyorhinis* ATCC 23234 | 0.05 | ≦0.01 | 0.1 | 0.5 | 0.25 | 0.025 | 0.1 | 0.1 | 0.25 | 0.5 | 0.5 | 0.25 |
| *M. hyorhinis* ATCC 25021 | 0.05 | ≦0.01 | 0.1 | 0.5 | 0.25 | 0.025 | 0.1 | 0.1 | 0.25 | 0.5 | 0.5 | 0.25 |
| *M. hyosynoviae* ATOC 25591 | <0.01 | 0.025 | 0.25 | 0.1 | 0.25 | 0.025 | 0.1 | 0.05 | 0.5 | 0.25 | 0.1 | 0.25 |
| *M. bovis* RCTC 10131 | <0.01 | ≦0.01 | 0.025 | 0.025 | 0.1 | ≦0.01 | ≦0.1 | <0.01 | ≦0.01 | ≦0.01 | 0.025 | ≦0.01 |
| *M. bovigenitalium* ATOC 14173 | <0.01 | ≦0.01 | 0.05 | 0.05 | 0.1 | ≦0.01 | ≦0.1 | 0.025 | ≦0.01 | 0.025 | 0.05 | 0.025 |
| M. dispar RCTC 10125 | 0.025 | 0.01 | 0.05 | 0.1 | 0.1 | ≦0.01 | 0.05 | 0.05 | 0.025 | 0.25 | 0.5 | 0.1 |
| *M. gallisepticum* S6 | 0.25 | 2.5 | >10.0 | >10.0 | 5.0 | 5.0 | 2.5 | 5.0 | 5.0 | 5.0 | 2.5 | 5.0 |
| *M. pneumoniae* ATCC 15492 | 0.1 | 1.0 | 5.0 | 10.0 | NG | 2.5 | 2.5 | NG | NG | 2.5 | 2.5 | 5.0 |

(b) Veterinary Bacteria

Table 2 shows the MIC values (μg/ml) of the compounds of the Examples against a number of organisms important in veterinary infections. The values were determined using a two fold serial dilutions in Diagnostic Sensitivity Test Agar with an inoculum of $10^4$ organisms and incubation for 18 hours at 37° C.

TABLE 2

| ORGANISMS | EXAMPLE NO - MIC (μg/ml) 1 | 2 | 3 | 4 | 5 | 6 | 7 | 8 | 9 | 10 | 11 | C |
|---|---|---|---|---|---|---|---|---|---|---|---|---|
| *E. Coli* NCTC 10418 | 40 | 40 | >80 | >80 | >80 | 80 | >80 | >80 | 80 | >80 | 80 | >80 |
| *E. Coli* E1 | 40 | 40 | >80 | >80 | >80 | 80 | >80 | >80 | 80 | >80 | 80 | >80 |
| *S. dublin* S7 | 40 | 80 | >80 | >80 | >80 | >80 | >80 | >80 | >80 | >80 | 80 | >80 |
| *S. typhimurium* S18 | 40 | 40 | >80 | >80 | >80 | 80 | >80 | >80 | 80 | >80 | 80 | >80 |
| *Bord. bronchiseptica* BO8 | 5 | 20 | >80 | >80 | >80 | 40 | 40 | 40 | 10 | 40 | 10 | 80 |
| *Bord. bronchiseptica* BO9 | 1.25 | 5 | 80 | 5 | 40 | 10 | 10 | 5 | 5 | 5 | 2.5 | 10 |
| *Past. multocida* PA1 | .156 | .615 | 20 | 5 | 10 | 1.25 | 2.5 | 1.25 | 0.625 | 2.5 | 0.625 | 2.5 |
| *Past. multocida* PA2 | >.019 | .312 | 2.5 | 2.5 | 2.5 | 0.625 | 1.25 | 1.25 | 0.156 | 0.625 | 0.156 | 1.25 |
| *Past. haemolytica* PA5 | 1.25 | 5 | 40 | 20 | 40 | 5 | 5 | 10 | 5 | 2.5 | 2.5 | 10 |
| *Erysipelothrix rhusiopathiae* NCTC 8163 | 10 | 20 | 80 | 40 | >80 | 20 | 10 | 20 | 40 | 20 | 5 | 80 |
| *Corynebacterium pyogenes* CY1 | >80 | >80 | >80 | >80 | >80 | >80 | >80 | >80 | >80 | >80 | >80 | >80 |
| *Staph. aureus* B4 | .156 | .625 | 2.5 | 2.5 | 2.5 | 0.312 | 0.625 | 0.625 | 0.625 | 0.625 | 0.156 | .625 |
| *Staph. aureus* 152 | .156 | .625 | 2.5 | 1.25 | 2.5 | 0.312 | 0.625 | 0.312 | 0.312 | 0.625 | 0.07 | .625 |
| *Staph. aureus* Oxford | .156 | .625 | 2.5 | 1.25 | 2.5 | 0.312 | 0.625 | 0.312 | 0.312 | 0.625 | 0.07 | .625 |
| *Strep. suis* (group D) SPS11 | 1.25 | 5 | 40 | 20 | 80 | 20 | 10 | 5 | 5 | 5 | 0.625 | 20 |
| *Strep. uberis* SPO1 | .039 | .07 | .312 | .312 | 0.625 | 0.07 | 0.156 | 0.07 | 0.156 | 0.312 | ≦0.019 | .07 |
| *Strep. dylgalactiae* SPD1 | .07 | .312 | 1.25 | .625 | 1.25 | 0.312 | 0.625 | 0.312 | 0.07 | 0.312 | 0.156 | .625 |
| *Strep. agalactiae SPA1* | .317 | .625 | 2.5 | 2.5 | 2.5 | 0.312 | 0.625 | 0.625 | 0.312 | 1.25 | 0.156 | 2.5 |

TABLE 2-continued

| ORGANISMS | EXAMPLE NO - MIC (μg/ml) | | | | | | | | | | | |
|---|---|---|---|---|---|---|---|---|---|---|---|---|
| | 1 | 2 | 3 | 4 | 5 | 6 | 7 | 8 | 9 | 10 | 11 | C |
| *B. subtilis* ATCC 6633 | NG | NG | NG | NG | NG | — | — | NG | NG | NG | NG | NG |

(c) Human Bacteria

Table 3 shows the MIC values (μg/ml) of the compounds of the Examples against a number of organisms important in human infections. The values were determined by serial dilutions in nutrient agar with 5% chocolated horse blood after incubations for 18 hours at 37° C.

TABLE 3

| ORGANISMS | EXAMPLE NO - MIC (μg/ml) | | | | | | | | | | | |
|---|---|---|---|---|---|---|---|---|---|---|---|---|
| | 1 | 2 | 3 | 4 | 5 | 6 | 7 | 8 | 9 | 10 | 11 | C |
| *E. coli* NCTC 10418 | 25 | >100 | >100 | >100 | >100 | 100 | >100 | >100 | 50 | >100 | >100 | >100 |
| *E. coli* ESS | 0.5 | 5.0 | 10 | 2.5 | 10 | 1.0 | 2.5 | 1.0 | 1.0 | 2.5 | — | 2.5 |
| *P. mirabilis* 889 | 100 | >100 | >100 | >100 | >100 | 100 | >100 | >100 | 50 | >100 | >100 | >100 |
| *K. aerogenes* A | 100 | >100 | >100 | >100 | >100 | 100 | >100 | >100 | 100 | >100 | >100 | >100 |
| *Ps. aeruginosa* NCTC 10662 | >100 | >100 | >100 | >100 | >100 | >100 | >100 | >100 | >100 | >100 | >100 | >100 |
| *Pasteurella multocida* 1633 | 0.5 | 10 | 25 | 10 | 25 | 0.5 | 5.0 | 2.5 | 2.5 | 2.5 | 5.0 | 2.5 |
| *Haemophilus influenzae* Q1 | 0.1 | 2.5 | 1.0 | 1.0 | 1.0 | 0.5 | 1.0 | 0.5 | 0.25 | 0.5 | 2.5 | 0.5 |
| *Haemophilus influenzae* Wy21 | — | — | — | — | — | 0.5 | 1.0 | — | 0.25 | 0.5 | — | — |
| *Neisseria catarrhalis* 1502 | — | 2.5 | 1.0 | 0.5 | 1.0 | <0.025 | 0.25 | 0.25 | 0.05 | 0.05 | 0.5 | 1.0 |
| *Bacillus subtilis* 6633 | 0.5 | 5.0 | 1.0 | 1.0 | 1.0 | 0.5 | 1.0 | 0.25 | 0.5 | 0.25 | 0.5 | 2.5 |
| *Corynebacterium xerosis* 9755 | >100 | >100 | >100 | >100 | >100 | >100 | >100 | >100 | >100 | >100 | >100 | >100 |
| *Sarcina lutea* 8340 | >100 | >100 | >100 | >100 | >100 | >100 | >100 | >100 | >100 | >100 | >100 | >100 |
| *Staph. aureus* Oxford | 0.5 | 10 | 2.5 | 2.5 | 2.5 | 0.5 | 1.0 | 2.5 | 1.0 | 1.0 | 1.0 | 2.5 |
| *Staph. aureus* Russell | 0.5 | 10 | 2.5 | 2.5 | 2.5 | 1.0 | 1.0 | 2.5 | 2.5 | 2.5 | 1.0 | 2.5 |
| *Staph. aureus* W2827 | 0.5 | 25 | 5.0 | 2.5 | 5.0 | 1.0 | 2.5 | 2.5 | 1.0 | 2.5 | 1.0 | 5.0 |
| *Strep. faecalis* 1 | 50 | >100 | >100 | >100 | >100 | >100 | >100 | 50 | 25 | >100 | 50 | >100 |
| *Strep. pyogenes* R80/421-A | 0.25 | 2.5 | 1.0 | 1.0 | 1.0 | 0.25 | 0.25 | 0.25 | 0.25 | 0.25 | 1.0 | 0.5 |
| Strep. 2733-B | — | 10 | — | 1.0 | — | 0.5 | 2.5 | — | 2.5 | 2.5 | 1.0 | 2.5 |
| Strep. 641848-C | 0.25 | — | 2.5 | 1.0 | 5.0 | 0.5 | 1.0 | 0.5 | 2.5 | 2.5 | 1.0 | — |
| *Strep. pneumoniae* CN33 | 0.1 | — | — | 1.0 | — | 0.25 | 0.5 | 0.5 | 2.5 | 2.5 | — | — |

The results in the Tables clearly show that m-motrobenzyl monate A has outstanding anti-mycoplasmal activity, being approximately 20 times more active against $M_1$-*suiphneumoniae* than O-nitrobenzyl monate A. Similarly, p-nitrobenzyl monate A has outstanding antibacterial activity as compared to o-nitrobenzyl monate A.

(d) *Treponema hyodysenteriae*

Table 4 shows the MIC values (μg/ml) of the compound of Example 1 against various strains of *Treponema hyodysenteriae,* which is important in swine dysentery. The value were obtained by the following method: The compound was incorporated in horse blood agar, inoculated (multi-point) with 0.001 ml of a 3 day growth of the test organism from base of a blood slope (+1 ml foetal calf serum) and incubated at 37° C. for 2 days under anaerobic conditions. The MIC was taken as the lowest concentration to inhibit β-haemolysis.

TABLE 4

Minimum Inhibitory Concentrations (μg/ml) for 5 strains of *Treponema hyodysenteriae*

| STRAIN NO. | MIC |
|---|---|
| S77/2 | 2.5 |
| S77/10 | 2.5 |
| P23 | 2.5 |
| Navis | 2.5 |
| B10 | 2.5 |

We claim:

1. A compound of formula (II):

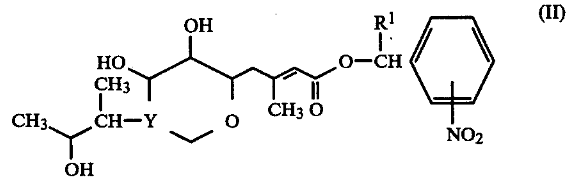

Y is

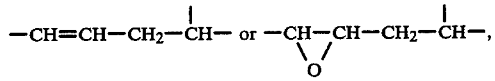

$R^1$ is hydrogen or $C_{1-4}$ alkyl, and the depicted nitro group is in the meta- or para-position on the benzene ring.

2. A compound as claimed in claim 1 wherein $R^1$ is hydrogen or methyl.

3. A compound selected from: p-nitrobenzyl monate A m-nitrobenzyl monate A 1-(m-nitrophenyl)ethyl monate A 1-(p-nitrophenyl)ethyl monate A and m-nitrobenzyl monate C.

4. A pharmaceutical or veterinary composition for treating mycoplasmal infections in humans and animals, comprising an effective amount of a compound according to claim 1 and a pharmaceutically acceptable carrier therefor.

5. A method for treating mycoplasmal infections in humans and animals which comprises administering an effective, non-toxic amount of a compound according to claim 1 to a human or animal having a micoplasmal infection.

6. A method for treating enzootic pneumonia in animals, which comprises administering an effective, non-toxic amount of a compound according to claim 1 to an animal having enzootic pneumonia.

7. A method for treating swine dysentery which comprises administering an effective, non-toxic amount of a compound according to claim 1 to a pig having swine disentery.

* * * * *